United States Patent
Shimizu et al.

(10) Patent No.: US 7,357,506 B2
(45) Date of Patent: Apr. 15, 2008

(54) EYE REFRACTIVE POWER MEASUREMENT APPARATUS

(75) Inventors: Kazunari Shimizu, Gamagori (JP); Yukinobu Ban, Nishio (JP); Toshiyuki Kawai, Toyohashi (JP)

(73) Assignee: Nidek Co., Ltd., Aichi-ken (JP)

( * ) Notice: Subject to any disclaimer, the term of this patent is extended or adjusted under 35 U.S.C. 154(b) by 33 days.

(21) Appl. No.: 11/388,144

(22) Filed: Mar. 24, 2006

(65) Prior Publication Data
US 2006/0244911 A1    Nov. 2, 2006

(30) Foreign Application Priority Data
Mar. 31, 2005    (JP)    ............... 2005-104610

(51) Int. Cl.
*A61B 3/10* (2006.01)
(52) U.S. Cl. ...................... 351/205; 351/211
(58) Field of Classification Search ............... 351/205, 351/206, 208, 211, 212, 216
See application file for complete search history.

(56) References Cited

U.S. PATENT DOCUMENTS

| | | | |
|---|---|---|---|
| 5,500,697 A | 3/1996 | Fujieda | |
| 6,217,172 B1 | 4/2001 | Shibutani et al. | |
| 6,547,392 B2 | 4/2003 | Fujieda | |
| 2005/0041210 A1* | 2/2005 | Isogai et al. | 351/205 |
| 2005/0146685 A1* | 7/2005 | Hanaki et al. | 351/200 |

FOREIGN PATENT DOCUMENTS

| | | |
|---|---|---|
| JP | A-7-39517 | 2/1995 |
| JP | A-2000-262475 | 9/2000 |
| JP | A-2001-275974 | 10/2001 |

* cited by examiner

*Primary Examiner*—Huy K Mai
(74) *Attorney, Agent, or Firm*—Oliff & Berridge, PLC

(57) ABSTRACT

An eye refractive power measurement apparatus capable of checking a presenting position (presenting distance) of a fixation target. The eye refractive power measurement apparatus has a measurement optical system for measuring eye refractive power of an examinee's eye, a fixation target presentation optical system for presenting a fixation target to the examinee's eye, a changing unit which changes a presenting position of the fixation target in a direction of an optical axis of the presentation optical system, a display, and a controller which controls to display a change of the presenting position as a diopter change on the display graphically.

6 Claims, 4 Drawing Sheets

EYE REFRACTIVE POWER MEASUREMENT APPARATUS

BACKGROUND OF THE INVENTION

1. Field of the Invention

The present invention relates to an eye refractive power measurement apparatus for measuring eye refractive power of an examinee's eye.

2. Description of Related Art

Conventionally, there is known an eye refractive power measurement apparatus for objectively measuring eye refractive power of an examinee's eye. This apparatus measures the eye refractive power of the examinee's eye in a no-accommodation (accommodation-pausing) state (i.e., a far-vision state) by changing a presenting position (presenting distance) of a fixation target on which the examinee's eye is fixated and fogging the examinee's eye. In addition, this apparatus measures the eye refractive power of the examinee's eye in an accommodation state (i.e., a near-vision state) by moving the presenting position (presenting distance) of the fixation target to a near position (near distance). In such measurement, it is convenient if it can be checked that the fixation target has been disposed at a presenting position (presenting distance) by which the examinee's eye can be brought to the no-accommodation state or at a presenting position (presenting distance) by which the examinee's eye can be brought to the accommodation state.

SUMMARY OF THE INVENTION

An object of the invention is to provide an eye refractive power measurement apparatus capable of checking a presenting position (presenting distance) of a fixation target.

To achieve the objects and in accordance with the purpose of the present invention, an eye refractive power measurement apparatus has a measurement optical system for measuring eye refractive power of an examinee's eye, a fixation target presentation optical system for presenting a fixation target to the examinee's eye, a changing unit which changes a presenting position of the fixation target in a direction of an optical axis of the presentation optical system, a display, and a controller which controls to display a change of the presenting position as a diopter change on the display graphically.

Additional objects and advantages of the invention are set forth in the description which follows, are obvious from the description, or may be learned by practicing the invention. The objects and advantages of the invention may be realized and attained by the eye refractive power measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
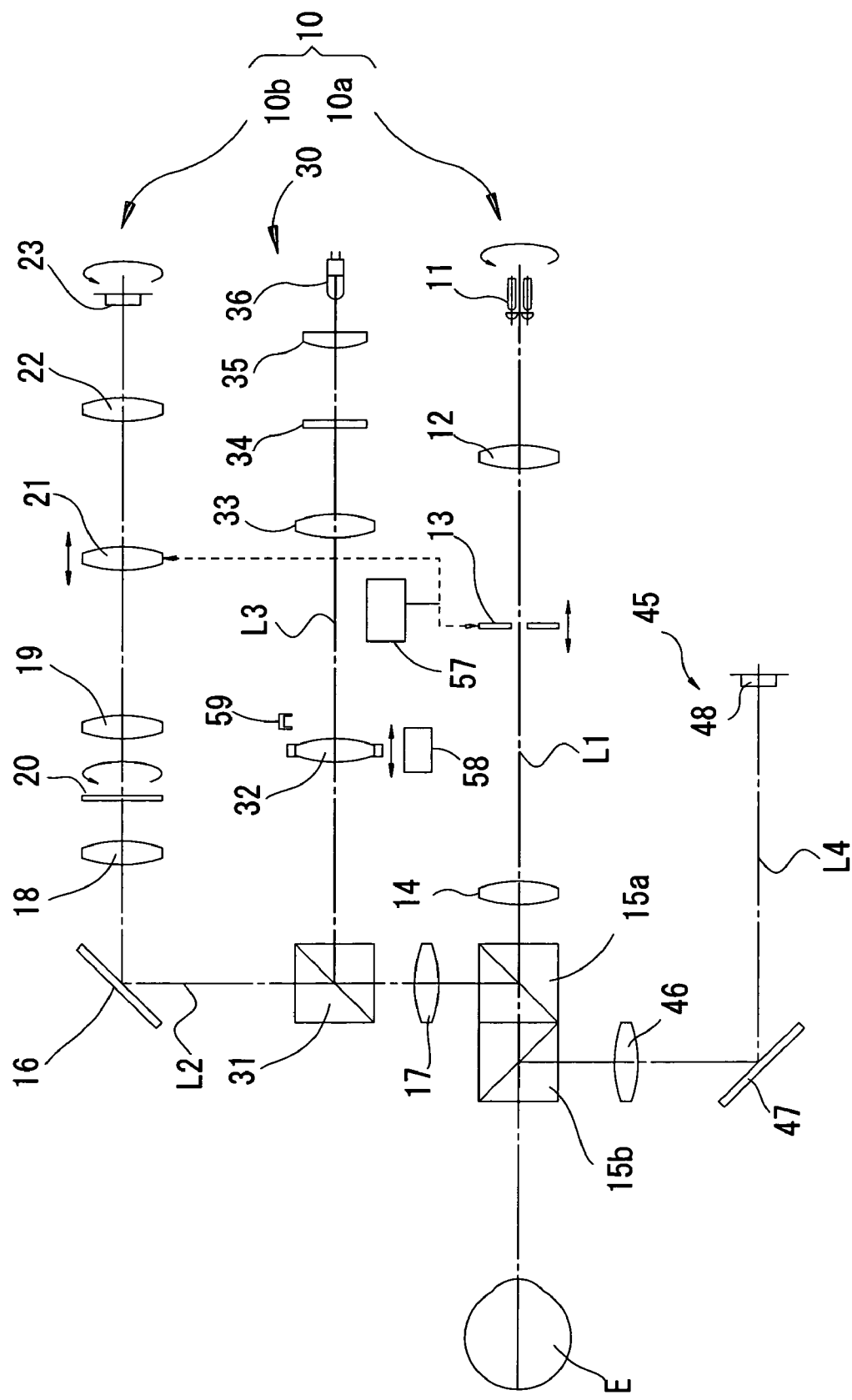
FIG. 1 is a view showing a schematic configuration of an optical system of an eye refractive power measurement apparatus consistent with the preferred embodiment of the present invention.

A detailed description of one preferred embodiment of an eye refractive power measurement apparatus embodied by the present invention is provided below with reference to the accompanying drawings. FIG. 1 is a view showing a schematic configuration of an optical system of an eye refractive power measurement apparatus consistent with the preferred embodiment of the present invention.

A measurement optical system 10 for projecting (throwing) a measurement target (measurement light bundle) onto a fundus of an examinee's eye E, receiving an image of (photo-receiving) the measurement target (measurement light bundle) reflected from the fundus, and objectively measuring eye refractive power of the examinee's eye E based on a result of the image-reception (photo-reception) includes an optical system 10a which projects (throws) the measurement target (measurement light bundle) and an optical system 10b which receives the image of (photo-receives) the reflected measurement target (measurement light bundle).

The optical system 10a, having an optical axis L1, includes two light sources 11 for measurement which emit infrared light, a condenser lens 12, a measurement target plate 13 with a measurement target (spot opening) having the optical axis L1 at the center, and a projection lens 14. The light sources 11 are disposed to be rotatable having the optical axis L1 as their center. In addition, the measurement target plate 13 is disposed to be movable on the optical axis L1 so as to be disposed at an approximately conjugate position with the fundus of the examinee's eye E.

The optical system 10b, having an optical axis L2, includes a half mirror 15a which makes the optical axis L2 and the optical axis L1 coaxial, an objective lens 17, a total reflection mirror 16, a relay lens 18, a corneal reflection removing mask 20 in a strip shape disposed at an approximately conjugate position with a cornea of the examinee's eye E, a relay lens 19, a mobile lens 21 disposed to be movable on the optical axis L2 in synchronization with the measurement target plate 13, an image forming lens 22, and a photodetector 23 for measurement. The mask 20 and the photodetector 23 are disposed to be rotatable having the optical axis L2 at their center in synchronization with the light sources 11.

The infrared measurement light bundle emitted from the light sources 11 passes through the lens 12 to the half mirror 15a and a half mirror 15b described later to be converged in the vicinity of the cornea of the examinee's eye E, and then reaches the fundus. If the examinee's eye is a normal eye, the measurement light bundle reflected from the fundus passes through the half mirror 15b to be reflected by the half mirror 15a, passes through the lens 17 and a half mirror 31 described later to be reflected by the mirror 16, and passes through the lens 18 to the lens 21 to form an image of the measurement target on the photodetector 23 by means of the lens 22. If the examinee's eye E has refractive error, based on a photo-receiving signal from the photodetector 23, the measurement target plate 13 is moved to the approximately conjugate position with the fundus so that the measurement target image is formed on the photodetector 23.

A fixation target presentation optical system 30 for presenting a fixation target on which the examinee's eye E is fixated, having an optical axis L3, includes the half mirror 31 which makes the optical axis L3 and the optical axis L2 coaxial, a first relay lens 32 disposed to be movable on the optical axis L3, a second relay lens 33, a fixation target 34 disposed at a focal point of the lens 33, a condenser lens 35, and an illumination light source 36 which emits visible light. In the presentation optical system 30, a presenting position (presenting distance) of the fixation target 34 is changed by moving the lens 32 in a direction of the optical axis L3. Owing to this, the examinee's eye E can be brought to a no-accommodation state by subjecting it to fogging or can be brought to an accommodation state by fixating it on the fixation target 34 presented at a near position (near distance). Incidentally, the change of the presenting position (presenting distance) of the fixation target 34 may be performed not only by moving the lens 32 but also by integrally moving the fixation target 34, the lens 35 and the light source 36. In addition, instead of the half mirror 31, a dichroic mirror which transmits the infrared light and reflects the visible light may be employed.

An observation optical system 45 for observing an anterior-segment of the examinee's eye E, having an optical axis L4, includes the half mirror 15b which makes the optical axis L4 and the optical axis L1 coaxial, an objective lens 46, a total reflection mirror 47, and a two-dimensional image-pickup element 48. An image of the anterior-segment of the examinee's eye E illuminated by an infrared light source for anterior-segment illumination not illustrated is reflected by the half mirror 15b and passes through the lens 46 to be reflected by the mirror 47 to be picked up by the image-pickup element 48.

Figure 2:
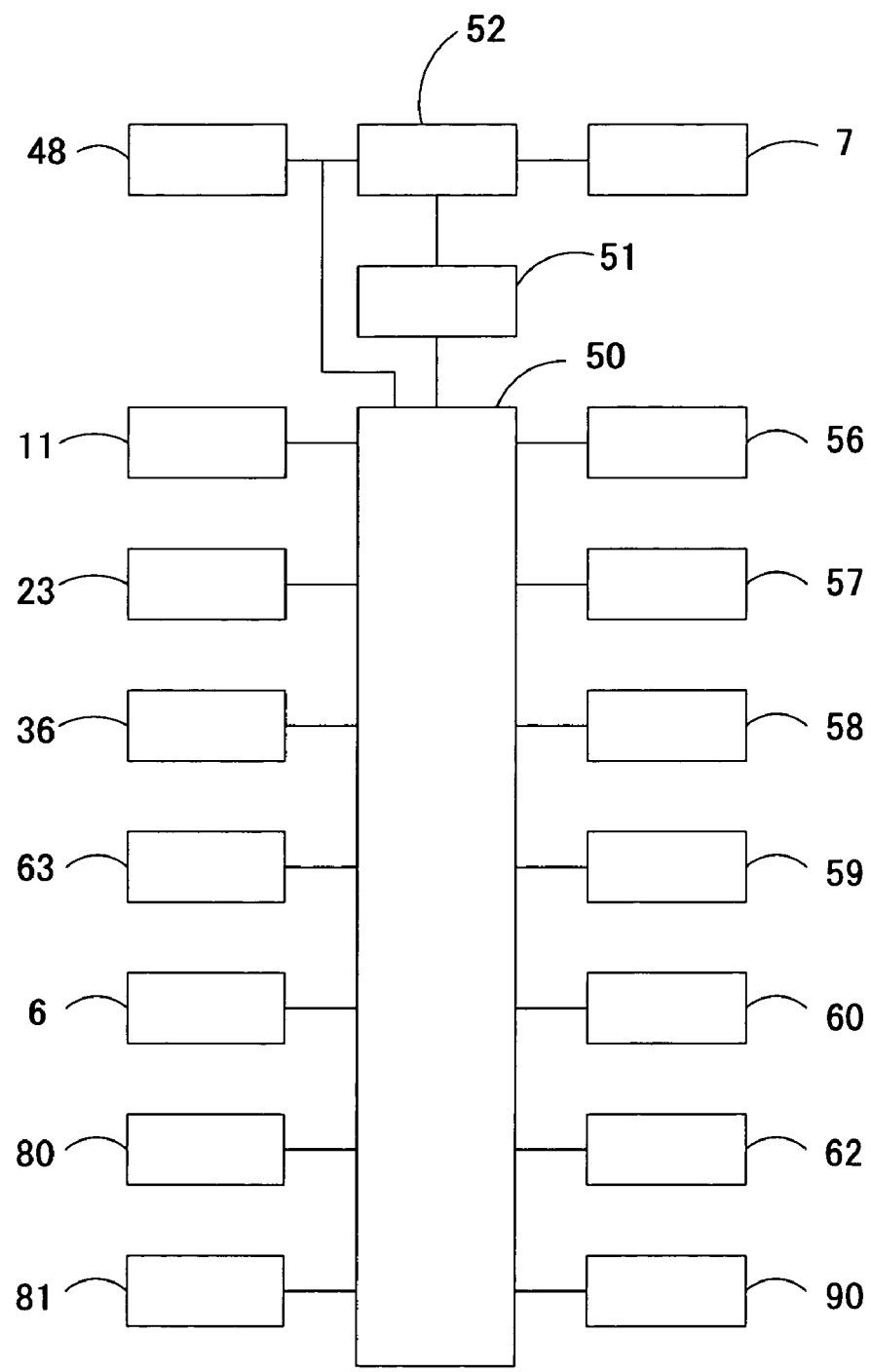
FIG. 2 is a schematic block diagram of a control system of the present apparatus.

FIG. 2 is a schematic block diagram of a control system of the present apparatus. An image signal from the image-pickup element 48 is synthesized by a synthesizing circuit 52 with signals of letters, graphics and the like produced by a display circuit 51 to be displayed on a monitor (display) 7. A calculation and control part 50 for controlling the entire apparatus is connected with the respective light sources including the light sources 11 and the light source 36, the photo detector 23, a rotation unit 56 such as a pulse motor which rotates the light sources 11, the mask 20 and the photo detector 23, a moving unit 57 such as a pulse motor which moves the measurement target plate 13 and the lens 21, a moving unit 58 such as a pulse motor which moves the lens 32, a photo-sensor 59, a potentiometer 60 which detects travel positions (travel distances) of the measurement target plate 13 and/or the lens 21, a memory 62, a printer 63, a measurement starting switch 6, a measurement mode changing switch 80, a fixation target moving switch 81, an input part (input unit) 90, and the like. The photo-sensor 59 detects that the lens 32 is placed at a reference position. The calculation and control part 50 obtains the travel position (travel distance) of the lens 32 based on the reference position and the number of pulses and the like for moving the lens 32, and obtains the presenting position (presenting distance) of the fixation target 34.

Next, an operation of the present apparatus will be described. First, a far-vision measurement mode of measuring the eye refractive power at far vision by which an eye is brought to the no-accommodation state is selected by means of the switch 80. When known alignment through observation of the anterior-segment image and the like of the examinee's eye E displayed on the monitor 7 is completed and a trigger signal for starting measurement is inputted by means of the switch 6, the calculation and control part 50 begins with preliminary measurement of the eye refractive power. Next, the calculation and control part 50 drives the moving unit 58 to move the lens 32 so that the fixation target 34 is disposed at a presenting position (presenting distance) corresponding to a far point of the examinee's eye E, and to further move the lens 32 so that fogging by an appropriate diopter is made to the examinee's eye E. Then, in the no-accommodation state in which the examinee's eye E is under fogging, the light sources 11, the mask 20 and the photodetector 23 are rotated 180 degrees at intervals of a predetermined angle (for example, 1 degree) During the rotation, the calculation and control part 50 controls to move the measurement target plate 13 and the lens 21 based on the photo-receiving signal from the photo detector 23, and calculates refractive power in respective directions of the rotation angles (in respective meridian directions) based on the travel positions (travel distances) of the measurement target plate 13 and/or the lens 21 detected by the potentiometer 60. Then, the calculation and control part 50 controls to subject the obtained refractive power to predetermined processing so as to calculate spherical power, astigmatic (cylindrical power) and an astigmatic (cylindrical) axial angle of the examinee's eye E at far vision.

In addition, the calculation and control part 50 controls to display the presenting position (presenting distance) of the fixation target 34 on the monitor 7. FIGS. 3A to 3D are views showing display examples of the presenting position (presenting distance) of the fixation target 34 in the process of the eye refractive power measurement at far vision. A graphic 70, which represents the presenting position (presenting distance) of the fixation target 34 as a diopter change, includes a base 70a showing a diopter range having 0 D (diopter) at the center (in this embodiment, a minus direction is presented on the left side (−20 D at the maximum) and a plus direction is presented on the right side (+20 D at the maximum), and a cursor 70b indicating an opposing presenting position (presenting distance) of the fixation target 34. The cursor 70b is arranged so that its display position is changed in accordance with virtual movement (hereinafter simply referred to as movement) of the fixation target 34 by the movement of the lens 32. In addition, the presenting position (presenting distance) of the fixation target 34 is displayed as a diopter also in a display box 71. Incidentally, in the display box 71, a desired presenting position (presenting distance) maybe inputted as a diopter by means of the input part 90 (a keyboard, a numeric keypad, or the like). When the presenting position (presenting distance) is inputted in the display box 71, the lens 32 is moved so that the fixation target 34 is disposed at the inputted presenting position (presenting distance) while the display position of the cursor 70b is changed. Alternatively, by arranging the display position of the cursor 70b to be changed by the input part 90 (a mouse, or the like), the lens 32 may be moved so that the fixation target 34 is disposed at a presenting position (presenting distance) based on a diopter of the display position. In this way, the presenting position (presenting distance) of the fixation target 34 may be designated on the monitor 7.

Figure 3A:
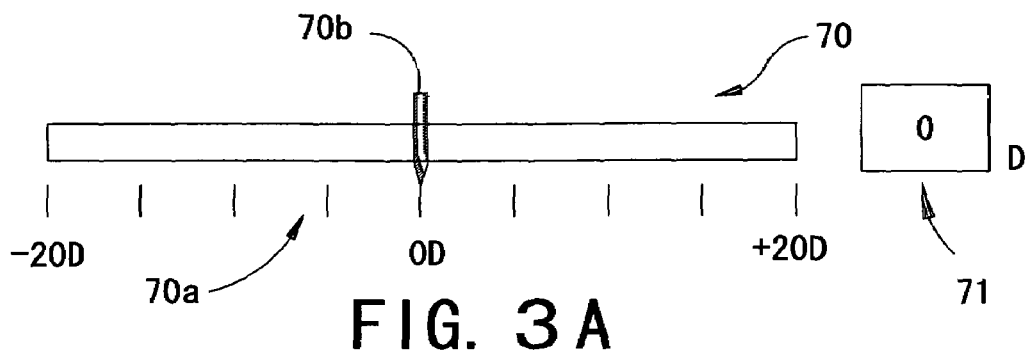
FIGS. 3A to 3D are views showing display examples of a presenting position (presenting distance) of a fixation target in the process of eye refractive power measurement at far vision.
Figure 3B:
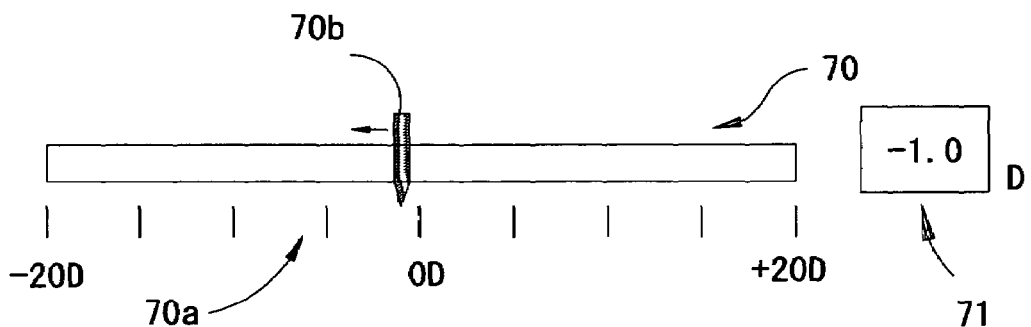
Figure 3C:
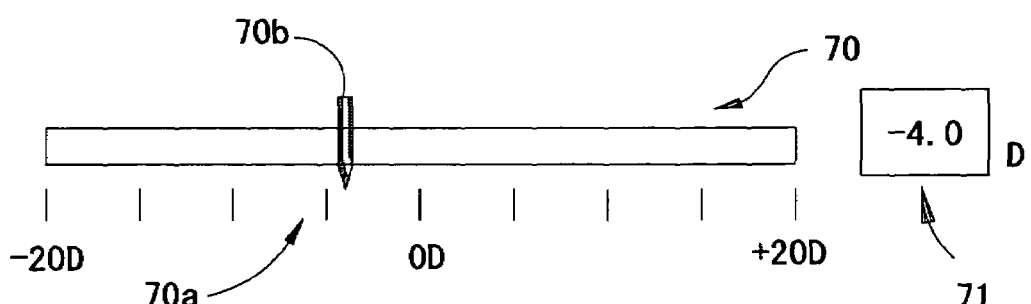
Figure 3D:
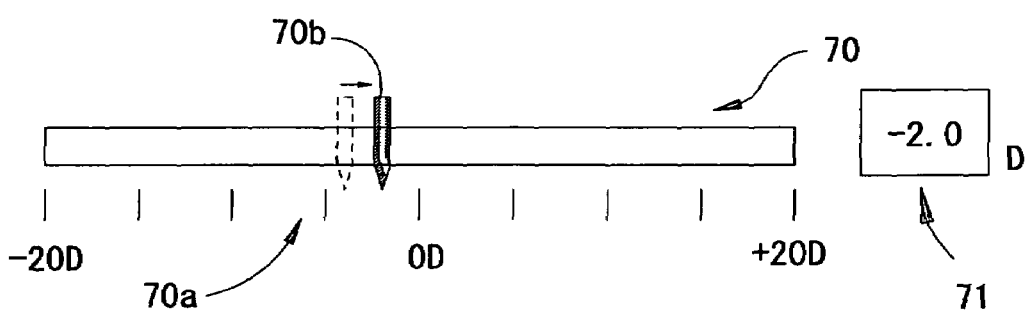

Once the preliminary measurement of the eye refractive power is performed and the lens 32 is moved so that the fixation target 34 is disposed at the presenting position (presenting distance) corresponding to the far point of the examinee's eye E based on the result of the preliminary measurement, the calculation and control part 50 controls to change the display position of the cursor 70b from the state in FIG. 3A through the state in FIG. 3B to the state in FIG. 3C. Thereafter, when the fixation target 34 (the lens 32) is moved so as to make fogging by an appropriate diopter, the calculation and control part 50 controls to change the display position of the cursor 70b from the state in FIG. 3C to the state in FIG. 3D.

Figure 4:
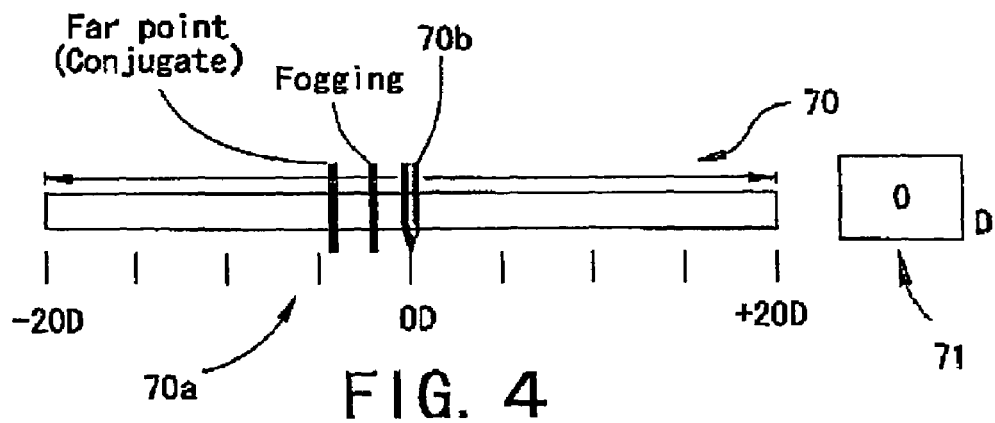
FIG. 4 is a view showing a display example of a presenting position (presenting distance) of the fixation target corresponding to a far point of an examinee's eye based on a result of preliminary measurement and a presenting position (presenting distance) of the fixation target when fogging is made to the examinee's eye.

Upon completion of the eye refractive power measurement at far vision, the calculation and control part 50 controls, in preparation for subsequent measurement, to move the lens 32 so that the fixation target 34 is disposed at a presenting position (presenting distance) equivalent to spherical equivalent power of the measured eye refractive power. Incidentally, after the completion of the measurement, such a display may be performed that the presenting position (presenting distance) corresponding to the far point of the examinee's eye E based on the result of the preliminary measurement and the presenting position (presenting distance) when fogging is made are conceivable, as shown in FIG. 4.

The display of the presenting position (presenting distance) of the fixation target 34 performed as mentioned above allows the presenting position (presenting distance) corresponding to the far point of the examinee's eye E based on the result of the preliminary measurement, the presenting position (presenting distance) when fogging is made, and the like to be checked. Accordingly, respective presenting positions (presenting distances) in a plurality of times of measurement (where measurement may be different in date and time) can be compared, whereby it can be checked if measurement has been performed at a proper presenting position (presenting distance). For example, in case the presenting position (presenting distance) of the fixation target 34 at the time of one measurement may be considerably different from the presenting position (presenting distance) at the time of another measurement, it can be known, before reaching a measurement result, that the presenting position (presenting distance) is not at a proper position (distance).

Incidentally, the presenting position (presenting distance) corresponding to the far point of the examinee's eye E based on the result of the preliminary measurement, the presenting position (presenting distance) when fogging is made, or the like may be displayed as a diopter in an additional display box.

In addition, after the completion of the measurement, the printer 63 may print out the presenting position (presenting distance) of the fixation target 34 along with the measurement result.

Next, a near-vision measurement mode of measuring the eye refractive power at near vision by which an eye is brought to the accommodation state is selected by means of the switch 80. In this mode, the fixation target 34 is moved to a desired near presenting position (presenting distance) by operation of the switch 81. When an operation signal from the switch 81 is inputted, the calculation and control part 50 drives the moving unit 58 to move the lens 32 so that the fixation target 34 is disposed at the near presenting position (presenting distance) For example, in order to make a presenting position (presenting distance) of the fixation target 34 equivalent to a near distance of 40 cm in the case of the spherical equivalent power to the previously measured eye refractive power at far vision being −3 D, the lens 32 is moved so that the fixation target 34 is disposed at a presenting position (presenting distance) corresponding to −5.5 D (−3 D-2.5 D). Besides, in the case of moving the fixation target 34 to the near presenting position (presenting distance), the movement is performed slowly so as to impose an accommodation load on the examinee's eye E with reliability. Then, with the examinee's eye E being under the accommodation load, the spherical power, the astigmatic (cylindrical) power and the astigmatic (cylindrical) axial angle) of the examinee's eye E at near vision are calculated in the same manner as the previous measurement at far vision.

Figure 5A:
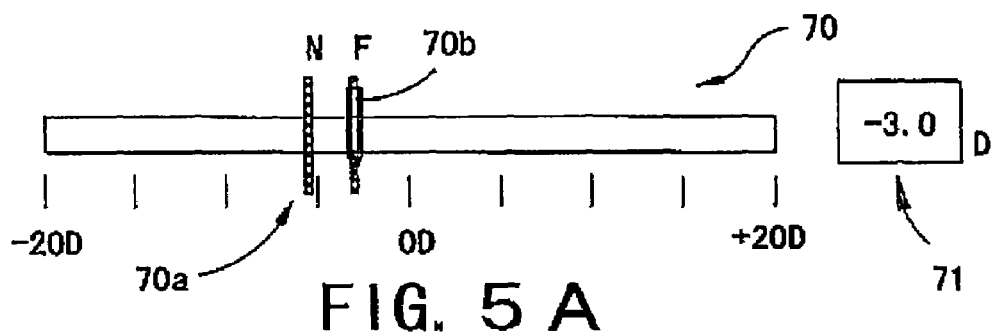
FIGS. 5A to 5C are views showing display examples of a presenting position (presenting distance) of the fixation target in the process of the eye refractive power measurement at near vision.
Figure 5B:
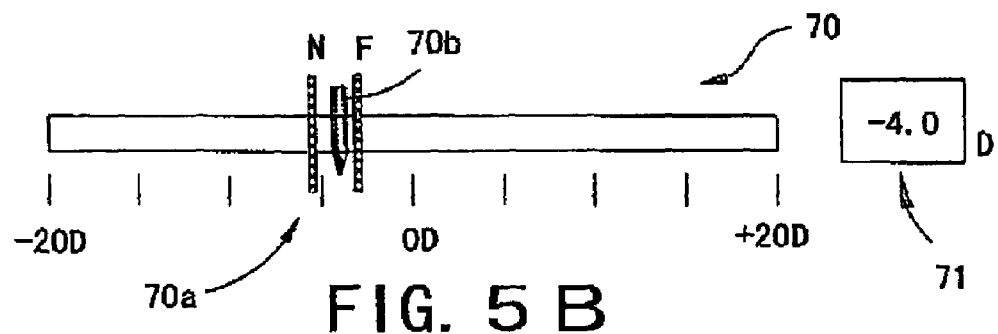
Figure 5C:
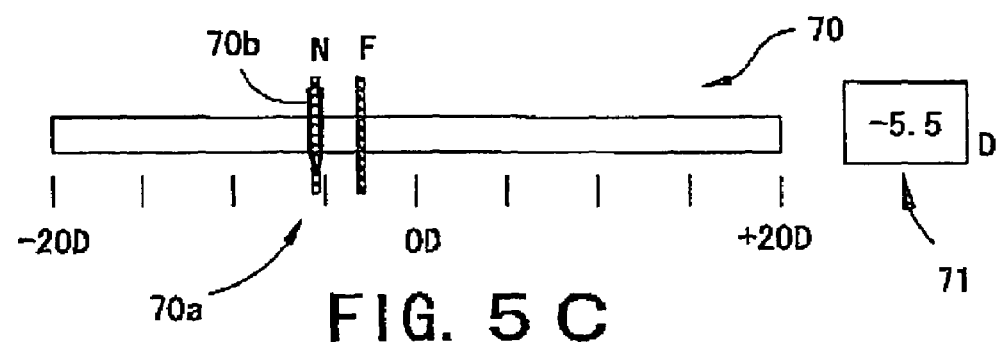

Besides, similar to the previous measurement at far vision, the calculation and control part 50 controls to display the presenting position (presenting distance) of the fixation target 34 on the monitor 7 also in the process of the measurement at near vision. FIGS. 5A to 5C are views showing display examples of the presenting position (presenting distance) of the fixation target 34 in the process of the eye refractive power measurement at near vision. The letter F represents a line indicating the presenting position (presenting distance) corresponding to the far point of the examinee's eye E, and the letter N represents a line indicating the near presenting position (presenting distance). Besides, a position of the line F can be set in accordance with the far point of the examinee's eye E based on the result of the preliminary measurement, the spherical equivalent power to the eye refractive power at far vision, and the like.

In the measurement at near vision, the presenting position (presenting distance) of the fixation target 34 is displayed on the monitor 7 in the following manner. For example, at the time of completing the measurement at far vision, the cursor 70b is displayed in alignment with the line F as shown in FIG. 5A. In the process of the movement of the fixation target 34 to the near presenting position (presenting distance), the cursor 70b is displayed between the line F and the line N as shown in FIG. 5B. Then, when the fixation target 34 reaches the near presenting position (presenting distance), the cursor 70b is displayed in alignment with the line N.

Owing to such display control, the process of the movement of the fixation target 34 to the near presenting position (presenting distance) can be checked. In other words, in the measurement at near vision, while it is difficult to know when the fixation target 34 has reached the near presenting position (presenting distance) since the fixation target 34 is slowly moved to the near presenting position (presenting distance), visual check of the movement process (the change of the presenting position (presenting distance)) of the fixation target 34 allows such difficulty to be cleared up.

Besides, while the fixation target 34 is moved to the near presenting position (presenting distance) by the operation of the switch 81 in the measurement at near vision, the presenting position (presenting distance) of the fixation target 34 may be designated on the monitor 7 in the same way as the previous measurement at far vision.

Incidentally, the present invention is applicable to an eye refractive power measurement apparatus in the broad sense of the term, such as an eye refractive power distribution measurement apparatus for measuring eye refractive power distribution in a wide range of an examinee's eye and a wavefront aberration measurement apparatus for measuring wavefront aberration of an examinee's eye. Then, by displaying a change of a presenting position (presenting distance) of a fixation target as a diopter change and an eye refractive power distribution map and the like, diagnosis of an accommodation change of the examinee's eye can be performed with accuracy and ease.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus comprising:
   a measurement optical system for measuring eye refractive power of an examinee's eye;
   a fixation target presentation optical system for presenting a fixation target to the examinee's eye;
   a changing unit which changes a presenting position of the fixation target in a direction of an optical axis of the presentation optical system;
   a display; and
   a controller which controls to display a change of the presenting position as a diopter change on the display graphically,
   wherein the controller controls to display as a diopter a first presenting position corresponding to a far point of the examinee's eye and a second presenting position changed from the first presenting position for making fogging to the examinee's eye on the display graphically.

2. The eye refractive power measurement apparatus according to claim 1, wherein the controller controls to display a measurable range as a diopter range on the display graphically.

3. The eye refractive power measurement apparatus according to claim 1, further comprising an input unit which inputs at least one of the presenting position and a presenting distance of the fixation target through graphic display on the display.

4. An eye refractive power measurement apparatus comprising:
   a measurement optical system for measuring eye refractive power of an examinee's eye;
   a fixation target presentation optical system for presenting a fixation target to the examinee's eye;
   a changing unit which changes a presenting position of the fixation target in a direction of an optical axis of the presentation optical system;
   a display; and
   a controller which controls to display a change of the presenting position as a diopter change on the display graphically,
   wherein the controller controls to display as a diopter a first presenting position corresponding to a far point of the examinee's eye and a third near presenting position closer to the examinee's eye than the first presenting position by a distance corresponding to a predetermined diopter on the display graphically.

5. The eye refractive power measurement apparatus according to claim 4, wherein the controller controls to display a measurable range as a diopter range on the display graphically.

6. The eye refractive power measurement apparatus according to claim 4, further comprising an input unit which inputs at least one of the presenting position and a presenting distance of the fixation target through graphic display on the display.

* * * * *